United States Patent [19]

Yamamoto et al.

[11] 4,054,053
[45] Oct. 18, 1977

[54] AUTOMATIC WELD FLAW DETECTOR

[75] Inventors: Eiji Yamamoto; Koji Ohta; Koji Sekiguchi; Toshiaki Fujimori, all of Tokyo, Japan

[73] Assignee: Tokyo Keiki Co., Ltd., Tokyo, Japan

[21] Appl. No.: 636,974

[22] Filed: Dec. 2, 1975

[30] Foreign Application Priority Data

Dec. 5, 1974 Japan .................... 49-139738

[51] Int. Cl.² .................................. G01N 29/04
[52] U.S. Cl. .................................. 73/67.8 S; 73/67.9
[58] Field of Search ............ 73/67.7, 67.8 R, 67.8 S, 73/67.9

[56] References Cited

U.S. PATENT DOCUMENTS

| 3,575,042 | 4/1971 | Lovelace | 73/67.8 S |
| 3,585,851 | 6/1971 | Walther | 73/67.8 S |
| 3,592,052 | 7/1971 | Giacomo et al. | 73/67.8 R |

OTHER PUBLICATIONS

E. Scott, Pictorial System for Charting Flaws, Ultrasonics, July 1966, pp. 152-156.

Primary Examiner—Richard C. Queisser
Assistant Examiner—John P. Beauchamp
Attorney, Agent, or Firm—Toren, McGeady and Stanger

[57] ABSTRACT

An automatic weld flaw detector comprises a comparator for comparing the height of an echo from a detected flaw upon movement of a probe over each unit distance with a maximum echo height already known, a counting circuit adapted to work in response to the comparing action of the comparator so as to determine the distance the probe has covered, a device adapted to be actuated by the output from the comparator thereby to memorize separately the maximum value of echo height and the output at that moment from the counting circuit, and a recorder connected to the memorizing device.

1 Claim, 5 Drawing Figures

AUTOMATIC WELD FLAW DETECTOR

BACKGROUND OF THE INVENTION

This invention relates to an automatic weld flaw detector which scans a weld with a probe for flaw detection and records the presence and location of any such flaw detected, all in automatic operation.

Where a conventional ultrasonic flaw detector of the pulse type is used to detect any flaw in a weld and determine its location, as illustrated in FIG. 1, its anglebeam probe P is caused to travel in zigzag fashion on a surface along and parallel to the weld so as to scan the joint thoroughly. In locating a detected flaw F, as shown in FIG. 2, the time axis of the ultrasonic detector is calibrated in advance so that the distance X between the point of incidence of the beam of ultrasonic waves upon the metal surface and the flaw F being detected can be directly read out. Also, the distance Y between the centerline 1 of the weld W and the point of incidence is measured. Then, from the known angle of refraction 0, the distance Z in the direction of depth of the flaw and the distance y from the centerline 1 of the weld W are calculated.

Although the flaw F present in the weld W may be located in the manner described, the procedure when followed manually would necessitate complicated calculation or even in automatic operation would require too large a calculating arragement, such as an electronic computer, to be practical. For the reasons stated, it has been customary, in automatic flaw detection, to record only the presence of any flaw detected and leave the location of the defect unreported.

However, knowing the location of a flaw in the weld is very important because the information will tell the type of the defect and furnish a basis for further evaluation. In addition, it will provide utmost ease of correction of the weld, if necessary.

SUMMARY OF THE INVENTION

Accordingly the primary object of this invention is to provide an automatic weld flaw detector which automatically examines a weld for flaw detection, finds the exact location of any such detected flaw by calculation, and records the results, all by simplified means. To accomplish the object of the invention a preferred embodiment thereof is in the form of an ultrasonic flaw detector comprising a comparator for comparing the amplitude of an echo from a detected flaw upon movement of a probe over each unit distance with a maximum echo amplitude already known, a counting circuit adapted to work in response to the comparing action of the comparator so as to determine the distance the probe has covered, means adapted to be actuated by the output from the comparator thereby to memorize separately the maximum value of echo amplitude and the output at that moment from the counting circuit, and a recorder connector to said memorizing means.

The automatic flaw detector according to the present invention further comprises a storage arrangement composed of a memory and a latch memory so as to memorize separately a maximum value obtained by comparing the height of echo reflected back from a detected flaw upon movement of the probe over each unit distance with the maximum echo previously determined and the distance covered by the probe when such a maximum value was obtained, whereby the exact location of the flaw in the weld can be readily output from the recorder. These features enable the operator to have a general idea of the internal flaw for further evaluation without resorting to an expensive, large electronic computer or the like but employing much less costly means. The flaw detector of the invention also permits the operator to take the necessary step, such as correction of the weld, adequately and efficiently.

The above and other objects, advantages and features of the invention will become more apparent from the following description taken in conjunction with the accompanying drawings.

DETAILED DESCRIPTION OF THE PREFERRED EMBODIMENTS

Figure 1:
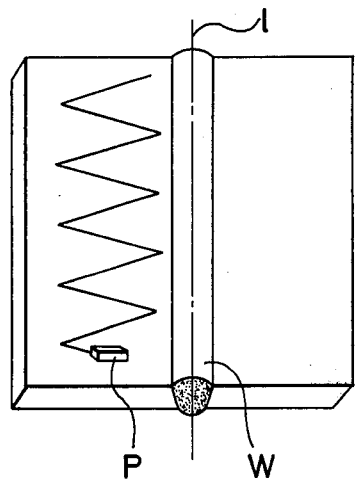
FIG. 1 is a perspective view of a welded joint with a probe traveling for ultrasonic flaw detection of the weld.
Figure 2:
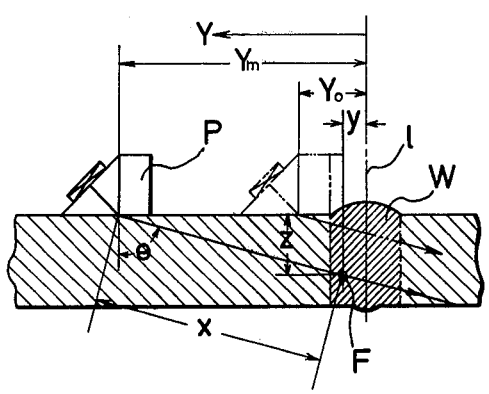
FIG. 2 is a fragmentary side view of the welded joint of FIG. 1, illustrating the relationship between a flaw present in the weld and the probe.
Figure 3:
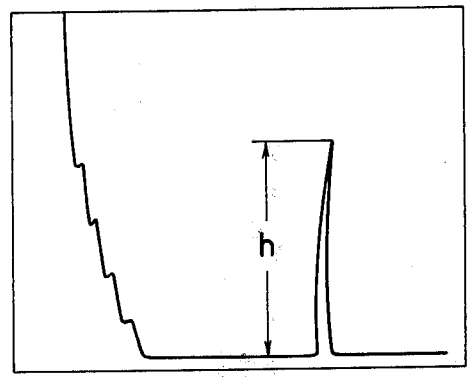
FIG. 3 is a graph showing an echo reflected back from a flaw in a weld.
Figure 4:
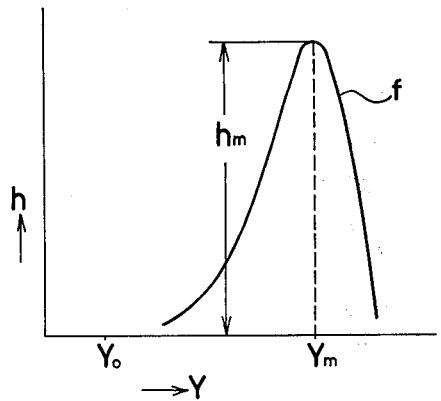
FIG. 4 is a graph showing a maximum echo from a flaw in a weld.

When, as shown in FIG. 2, the distance Z in the direction of depth of a flaw F present in a weld W is to be determined using an ultrasonic flaw detector in accordance with the present invention, a probe P is caused to move zigzag from a starting point at a distance Yo from the centerline $l$ of the weld so as to vary the distance Y between the probe P and the centerline $l$ while scanning the weld across the centerline. The time axis is calibrated beforehand in order that the distance X between the flaw F and the incidence point of the ultrasonic wave beam be directly read out at any point of the scanning operation. Thus, the intensity lever, or amplitude or height $h$, of echoes $f$ reflected back from the flaw F will be as graphically shown in FIG. 3. It will be appreciated that, given the distance Y between the originating point of ultrasonic scanning and the point where the height $h$ of the echoes $f$ reaches a peak, or the distance $Y_m$, then the distance Z in the direction of depth of the flaw F would be readily determined by calculation on the basis of the known refraction angle $\theta$ of the ultrasonic beam. The refraction angle usually is large, in the neighborhood of 70°. Since the width ofthe weld W is limited, the distance Z may be considered directly proportional to the distance Y.

Figure 5:
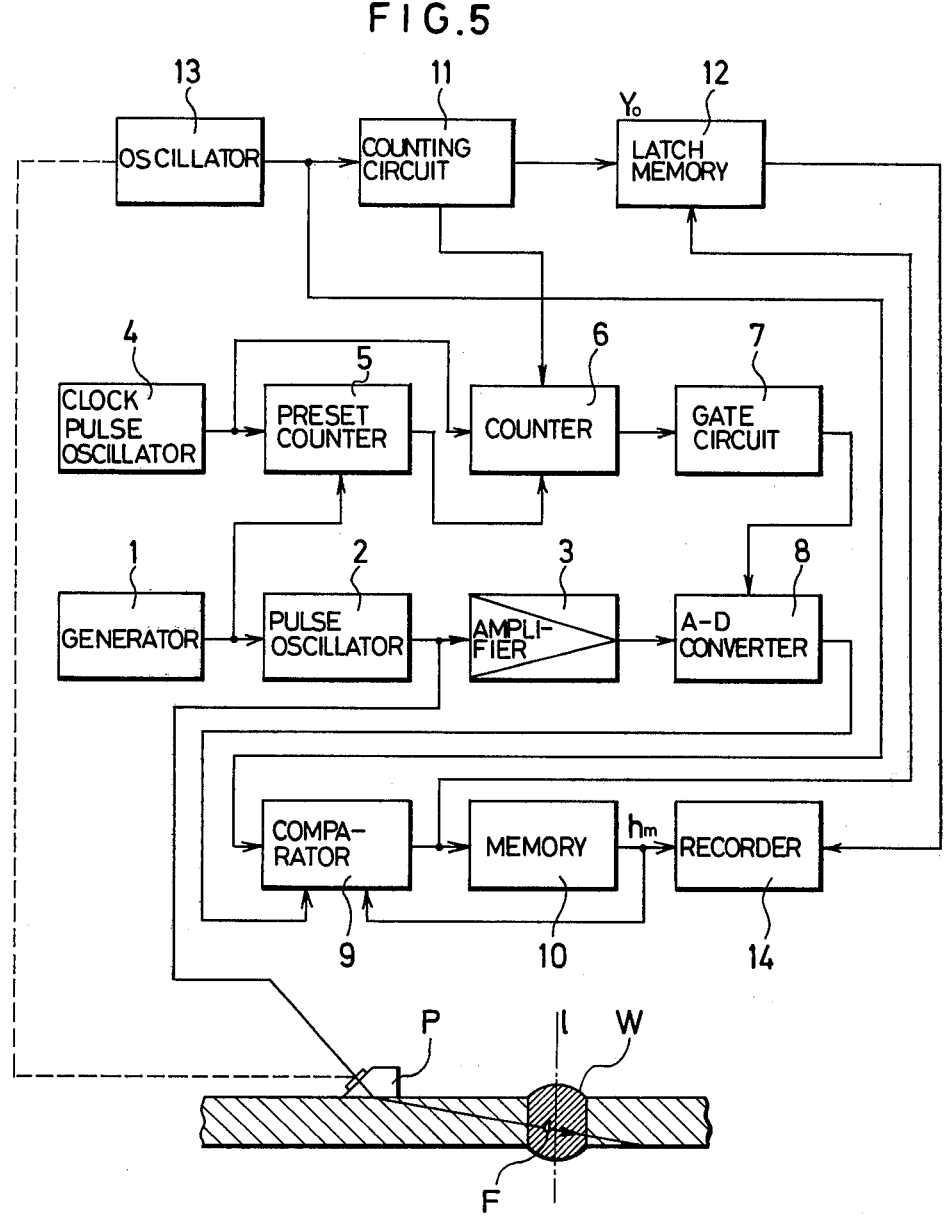
FIG. 5 is a block diagram of an embodiment of the automatic weld flaw detector of the invention.

FIG. 5 is a block diagram of the arrangement embodying the invention for locating a defect F of a weld W and recording the location. In the figure, 1 is a synchronizing signal generator for the timing of the system operation, 2 is a high-voltage pulse oscillator, and 3 is a reception amplifier. These components are of known constructions and the detailed description is omitted. Numeral 4 designates a clock pulse oscillator for producing clock pulses of a frequency corresponding to the acoustic velocity, and 5 designates a preset counter for counting the clock pulses in response to the synchronizing signals. The counter 5 will continue counting until, as shown in FIG. 2, the beam of ultrasonic waves originated from the probe P in the position at a distance Yo from the weld centerline and reflected as echoes from the weld W returns to the probe P.

The count (preset number) of this preset counter 5 is established as follows.

It is possible to calculate the round trip or reciprocating time of reciprocation of the beam of ultrasonic waves between the probe P and the weld W by considering the distance of the probe P as a known value, the propagation speed, and the refraction angle $\theta$ of the ultrasonic beam. On the other hand, the frequency of the aforesaid clock pulse is already known. Accordingly, the round-trip or reciprocating time of the ultrasonic beam can be expressed in terms of the clock pulses.

Therefore, the preset counter 5 is manually preset and adjusted so that the number of clock pulses corresponding to the round-trip time of the beam may be calculated. A counter 6 is adapted to commence its action by an output when the preset counter 5 has counted clock pulses up to the aforesaid preset count and likewise to count the clock pulses. Thereupon, for example, when the probe P has moved a unit distance from a position $Y_o$ in FIG. 2 in the direction of Y, the round-trip time of the ultrasonic beam to its return to the probe P will naturally be longer than the round-trip time of the beam when the probe P is positioned at the distance of $Y_o$. The aforesaid counter 6 is provided for the purpose of adding the increase in the round trip time of the beam upon movement of the probe P to the counted time of said preset counter 5.

This count is controlled by the counter circuit 11, described later, for measuring the amount of movement of the probe P. Moreover, when the probe moves in the direction reverse to Y direction of FIG. 2, said counter 6 deducts from the counter 5.

Numeral 7 indicates a gate circuit which is actuated upon receiving an output of the counter 6. The width of gate of the gate circuit 7 is preset so as to coincide with the round trip time of the ultrasonic beam in the weld W. Numeral 8 indicates an A-D converter which is adapted to quantize digitally a flaw detection signal input from the amplifier 3. The converter 8 is adapted to act for as long as the gate of said gate circuit is open. A comparator 9 compares a flaw echo amplitude at a time of an output from the A-D converter 8 with a maximum flaw echo amplitude memorized by the memory circuit 10, explained later, which was detected before the time of the output. Then, only when the flaw echo amplitude from said converter 8 exhibits a value larger than the maximum echo amplitude, the value of the former is applied to the memory circuit 10. Moreover, this comparator 9 is designed to commence its comparing action upon receiving a signal from an oscillator 13 which will be explained later on.

The memory circuit 10, is adapted to memorize a value before a point of time when a comparing signal value is applied from the comparator 9 in exchange for the comparing signal. Numeral 11 denotes the counting circuit, 12 a latch memory circuit, and 14 a recorder. The oscillator 13 produces one pulse per movement of the probe P for a unit distance and each ouput pulse is applied to the counting circuit 11. Accordingly, the content of the counting circuit 11 shows the position of the probe P and the content is applied to the counter 6 and the latch memory circuit 12.

The latch memory circuit can memorize the counting content of the counting circuit 11 only when an output signal has been issued from said comparator 9 and then the memorized content is transferred to said recorder 14.

Accordingly the content memorized by the memory circuit 10 indicates a flaw echo amplitude at the position of the probe P which is memorized by said latch memory circuit 12. In the flaw detecting apparatus of the present invention, when the probe P has moved a unit distance from the position $Y_\theta$ and in the direction Y as shown in FIG. 2, the oscillator 13 produces a pulse corresponding to the amount of movement of the probe P, and this pulse is counted by said counting circuit 11.

Then the counting circuit 11 produces a signal of indication of position of the probe P to said counter 6 and the latch memory circuit 12 respectively.

On the other hand, the preset counter 5 counts the clock pulse from the clock pulse oscillator 4 and transfers an output signal to the counter 6 at the point of time of counting said clock pulse, whereby said counter 6 commences the counting of the clock pulse from said oscillator 4. At this instant, since the signal from said counting circuit 11 is input applied, the point of time of output signal from said counter 6 is sure to coincide with the point of time of reciprocation of the ultrasonic beam between the probe P, which has moved a unit distance, and the front edge of the weld W. Subsequently, the gate circuit 7 receives an output from said counter 6 and actuates A - D converter 8 for the aforesaid gate time. Out of the constituents of the signal input into the converter 8 from the amplifier 3, only the echo signal of ultrasonic wave beam having passed through the weld W can be extracted and quantized by the converter 8. Accordingly, the echo signal output from said converter 8 represents the echo F of the flaw F preset in the weld W and the amplitude of said echo F is applied to the comparator 9. And the amplitude h of the echo f input into said comparator 9 is compared with the contents already memorized by the memory circuit 10, namely, the amplitude hm of the echo which was detected when the probe P was positioned at the distance Y.

In this case, if $h > hm$, the height $h$ of the echo is memorized by the memory circuit 10 as the maximum amplitude $hm$ of flaw echo at the present instant.

Simultaneously, the output signal from the comparator 9 causes the latch memory circuit 12 to memorize the position of the probe P at the present time and the value thus memorized to be applied to the recorder 14. In addition, as the result of comparison at said comparator 9, if $h < hm$, there is no output from said comparator 9 and consequently there is no occasion for rewriting of memorized contents of the memory circuit either. Nor is there any output from the latch memory circuit 12.

In this way, by moving the probe P in turn for a unit distance, it is possible for the recorder automatically to record the maximum echo amplitude $hm$ of flaw and the position of the probe at the time of movement of the probe P.

Due to the above, it is also possible automatically to detect and record the maximum echo amplitude $hm$ of a flaw in the weld W and the distance $Y_m$ between the probe P and the central line of the weld W by dint of the probe's scanning for one time. Thus, on the basis of flaw detection data obtained by the recorder 14, it is possible to determine the position of said flaw F relative to the central line $l$ and the depth Z.

The distance X can be obtained by dividing the time of ultrasonic wave beam moving from the probe P positioned at the distance $Y_m$ and reaching the flaw F by the speed of said ultrasonic wave beam. (Said time can easily known by wave-form observation with a cathode ray tube with the result that said position Y is obtained as $Y = Y_m - X \sin \theta$ and the depth Z as $Z = X \cos \theta$.

We claim:

1. An automatic weld-flaw detecting apparatus, which comprises a probe movable along a welded member for applying and detecting ultrasonic waves, a memory for memorizing the amplitude of the echoes, a comparator coupled to the memory and the probe for repeatedly comparing an echo amplitude after each movement of the probe for a unit distance with the content of the memory and applying the larger of the compared amplitude to the memory, said memory memorizing only the larger of the compared amplitudes, a source of clock pulses, a counting circuit responsive to the distance of movement of said probe, a first counter set for counting clock pulses over a period of time corresponding to the time a beam of ultrasonic wave from the probe takes to reach a weld portion and its echo returns to said probe, a second counter coupled to the first counter and adapted to commence in response to said first counter having counted clock pulses up to the set value and stop counting in response to the content of said counting circuit, a gate circuit opened only between the stop and start of clock pulses from said second counter, an A-D converter responsive to said probe for applying the echo amplitude of the flaw into said comparator upon receiving control of said gate circuit, a latch memory circuit responsive to said comparator and said counting circuit for memorizing the contents of said counting circuit at the time of memory of the maximum flaw echo amplitude by said memory and a recorder for recording each of the contents of said latch memory circuit, and the memory circuit, and whereby it is made possible automatically to record a maximum value of flaw echo amplitude in a weld portion and the distance between the probe and the weld portion during each scan by said probe.

* * * * *